US011037665B2

(12) United States Patent
O'Keeffe et al.

(10) Patent No.: US 11,037,665 B2
(45) Date of Patent: Jun. 15, 2021

(54) GENERATING MEDICATION ORDERS FROM A CLINICAL ENCOUNTER

(71) Applicant: International Business Machines Corporation, Armonk, NY (US)

(72) Inventors: William G O'Keeffe, Boulder City, NV (US); Ahmed Al Dulaimy, Covington, WA (US)

(73) Assignee: International Business Machines Corporation, Armonk, NY (US)

( * ) Notice: Subject to any disclaimer, the term of this patent is extended or adjusted under 35 U.S.C. 154(b) by 441 days.

(21) Appl. No.: 15/867,895

(22) Filed: Jan. 11, 2018

(65) Prior Publication Data

US 2019/0214121 A1  Jul. 11, 2019

(51) Int. Cl.
| | |
|---|---|
| *G16H 20/10* | (2018.01) |
| *G16H 10/60* | (2018.01) |
| *G16H 50/20* | (2018.01) |
| *G06N 20/00* | (2019.01) |
| *G16H 50/50* | (2018.01) |
| *G16H 40/63* | (2018.01) |

(52) U.S. Cl.
CPC ............ *G16H 20/10* (2018.01); *G06N 20/00* (2019.01); *G16H 10/60* (2018.01); *G16H 40/63* (2018.01); *G16H 50/20* (2018.01); *G16H 50/50* (2018.01)

(58) Field of Classification Search
CPC ........ G16H 20/10; G16H 50/50; G16H 10/60; G16H 50/20; G16H 40/63; G06N 20/00
See application file for complete search history.

(56) References Cited

U.S. PATENT DOCUMENTS

| | | | | |
|---|---|---|---|---|
| 10,032,127 | B2* | 7/2018 | Habboush | G06N 20/00 |
| 10,607,728 | B2* | 3/2020 | Agassi | G16H 10/60 |
| 2002/0042726 | A1* | 4/2002 | Mayaud | G06F 19/3456 |
| | | | | 705/2 |
| 2003/0061054 | A1* | 3/2003 | Payne | G10L 15/26 |
| | | | | 704/277 |
| 2003/0120517 | A1 | 6/2003 | Eida et al. | |
| 2007/0299665 | A1 | 12/2007 | Koll et al. | |
| 2009/0119095 | A1* | 5/2009 | Beggelman | G06F 40/30 |
| | | | | 704/9 |
| 2011/0301982 | A1 | 12/2011 | Green, Jr. et al. | |

(Continued)

OTHER PUBLICATIONS

Deleger et al., "Extracting medical information from narrative patient records: the case of medication-related information," Journal of the American Medical Informatics Association, Sep.-Oct. 2010, 17(5): 555-558.

(Continued)

*Primary Examiner* — Jonathan Durant
*Assistant Examiner* — Anne-Marie K Alderson
(74) *Attorney, Agent, or Firm* — Patterson + Sheridan, LLP

(57) ABSTRACT

Performing an operation comprising applying one or more natural language processing (NLP) algorithms to a text transcription of a medical encounter dialogue to determine a plurality of features of the dialogue, processing, by a machine learning (ML) model executing on a processor, the text transcription and the plurality of features of the dialogue to identify a plurality of candidate medications from a knowledge base corresponding to a first statement made by a medical professional during the medical encounter, and outputting an indication of the plurality of candidate medications for display.

20 Claims, 9 Drawing Sheets

(56) References Cited

U.S. PATENT DOCUMENTS

| | | | |
|---|---|---|---|
| 2013/0238329 A1* | 9/2013 | Casella dos Santos | ................... G16H 15/00 704/235 |
| 2015/0379200 A1* | 12/2015 | Gifford | ................ G16H 10/60 705/3 |
| 2017/0242919 A1* | 8/2017 | Chandramouli | .... G06F 16/9535 |
| 2018/0373844 A1* | 12/2018 | Ferrandez-Escamez | ................... G06F 40/284 |
| 2019/0163875 A1* | 5/2019 | Allen | ................... G06F 40/295 |

OTHER PUBLICATIONS

Zhou et al, "Using Medical Text Extraction, Reasoning and Mapping System (MTERMS) to Proces Medication Information in Outpatient Clinical Notes," AMIA Annual Symposium Proceedings Archive, 2011; 2011: 1639-1648.

\* cited by examiner

Doctor: So, how can I help you today?
Patient: Well, em, I've been having pains in my chest and upper back. I can't tell if it's just muscle pain or if it might be my heart. So I figured I should get it checked out just in case.
Doctor: How long has this been going on?
Patient: Just a couple of days.
Doctor: Have you had any shortness of breath or difficulty breathing?
Patient: Nope. I was pretty breathless watching that game last night though. That was amazing. Did you see it?
Doctor: ha! Of course, that was a nail biter! I was at a restaurant and considered handing out medicine Y to calm people down.
Patient: [Laugh]
Doctor: Well, everything looks good with your heart and lungs, EKG is normal. However it looks like your blood pressure is still higher than I would like it to be. We should try to bring that down. Let's try increasing the dose of the your blood pressure meds and I'll bring you back in a month to see how you're progressing. I'd rather have you on a higher dose of the beta blockers than putting you on an ACE as well.
Patient: OK, that works for me.
Doctor: You don't take these pills with alcohol right? And you know to take them after meals, correct?
Patient: Sure do.
Doctor: Ok, great. Let me show you out. The nurse will have your prescription up front.
Patient: Thanks, have a great day.
Doctor: You too, bye now.

FIG. 2A

Doctor [Normal]: *So, how can I help you today?*
Patient [Concerned, Nervous]: ~~Well, em,~~ I've been having pains in my chest and upper back. I can't tell if it's just muscle pain or if it might be my heart. So, I figured I should get it checked out just in case.
Doctor [Normal]: *How long has this been going on ?*
Patient [Normal]: *Just a couple of days.*
Doctor [Normal]: *Have you had any shortness of breath or difficulty breathing?*
Patient [Joking, Excited]: *Nope. I was pretty breathless watching that game last night though. That was amazing. Did you see it ?*
Doctor [Joking, Excited]: ~~ha!~~ *Of course. That was a nail biter!* I was at a restaurant and considered handing out medicine Y to calm people down.
Patient ~~[Joking]: [Laugh]~~
Doctor [Normal]: *Well, everything looks good with your heart and lungs, EKG is normal. However it looks like your blood pressure is still higher than I would like it to be. We should try to bring that down.* Let's try to increasing the dose of your blood pressure meds and I'll bring you back in a month to see how you're progressing. I'd rather have you on a higher dose of the beta blockers than putting you on an ACE as well.
Patient [Normal]: *OK, that works for me.*
Doctor [Normal]: You don't take these pills with alcohol right ? And you know to take them after meals, correct ?
Patient [Normal]: *Sure do.*
Doctor [Normal]: *OK, great. Let me show you out. The nurse will have your prescription up front.*
Patient [Normal]: *Thanks, have a great day.*
Doctor [Normal]: *You too, bye now.*

210 — Doctor [Joking, Excited] [Watching Sports]: I was at a sports bar and considered handing out medicine Y to calm people down.

211 — Doctor [Normal] [Heart Condition, Hypertension]: Let's try increasing the dose of the your blood pressure meds and I'll bring you back in a month to see how you're progressing. I'd rather have you on a higher dose of the beta blockers than putting you on an ACE as well.

212 — Doctor [Normal] [Heart Condition, Hypertension]: You don't take these pills with alcohol right? And you know to take them after meals, correct?

213 — Doctor [Normal] [Heart Condition, Hypertension]: The nurse will have your prescription up front.

GENERATING MEDICATION ORDERS FROM A CLINICAL ENCOUNTER

BACKGROUND

The present invention relates to computing systems, and more specifically, to computing systems which generate medication orders from clinical encounters.

Conventionally, medical professionals must spend time and resources to prescribe medications for patients. For example, for a prescription, a physician must write, call, and/or electronically provide an indication of the prescription to a pharmacy. Often, the physician may delegate the task to others. In any event, these manual operations waste time and resources, and may lead to errors. Reducing the time needed to prescribe a medication would increase the amount of time medical professionals have to interface with patients and increase the overall quality of patient care.

SUMMARY

According to one embodiment, a computer-implemented method comprises applying one or more natural language processing (NLP) algorithms to a text transcription of a medical encounter dialogue to determine a plurality of features of the dialogue, processing, by a machine learning (ML) model executing on a processor, the text transcription and the plurality of features of the dialogue to identify a plurality of candidate medications from a knowledge base corresponding to a first statement made by a medical professional during the medical encounter, and outputting an indication of the plurality of candidate medications for display.

In another embodiment, a system comprises a processor and a memory storing instructions, which when executed by the processor, performs an operation comprising applying one or more natural language processing (NLP) algorithms to a text transcription of a medical encounter dialogue to determine a plurality of features of the dialogue, processing, by a machine learning (ML) model, the text transcription and the plurality of features of the dialogue to identify a plurality of candidate medications from a knowledge base corresponding to a first statement made by a medical professional during the medical encounter, and outputting an indication of the plurality of candidate medications for display.

In another embodiment, a computer-readable storage medium has computer-readable program code embodied therewith, the computer-readable program code executable by a processor to perform an operation comprising applying one or more natural language processing (NLP) algorithms to a text transcription of a medical encounter dialogue to determine a plurality of features of the dialogue, processing, by a machine learning (ML) model, the text transcription and the plurality of features of the dialogue to identify a plurality of candidate medications from a knowledge base corresponding to a first statement made by a medical professional during the medical encounter, and outputting an indication of the plurality of candidate medications for display.

BRIEF DESCRIPTION OF THE SEVERAL VIEWS OF THE DRAWINGS

FIGS. 2A-2C illustrate example text transcriptions generated based on a clinical encounter, according to one embodiment.

DETAILED DESCRIPTION

Embodiments disclosed herein provide techniques to extract medication information from a transcript of a clinical encounter with higher accuracy than conventional approaches. Generally, embodiments disclosed herein leverage speech to text algorithms to transcribe an encounter between a medical professional (e.g., a physician, nurse practitioner, nurse, etc.) and a patient in real time. Embodiments disclosed herein then apply NLP and ML techniques to extract medication information, which can be presented to the medical professional as candidate medications. The medical professional may then select one or more candidate medications for the patient. In the case of medications requiring a prescription, embodiments disclosed herein may transmit an indication of the prescription to a pharmacy for fulfillment.

Figure 1:
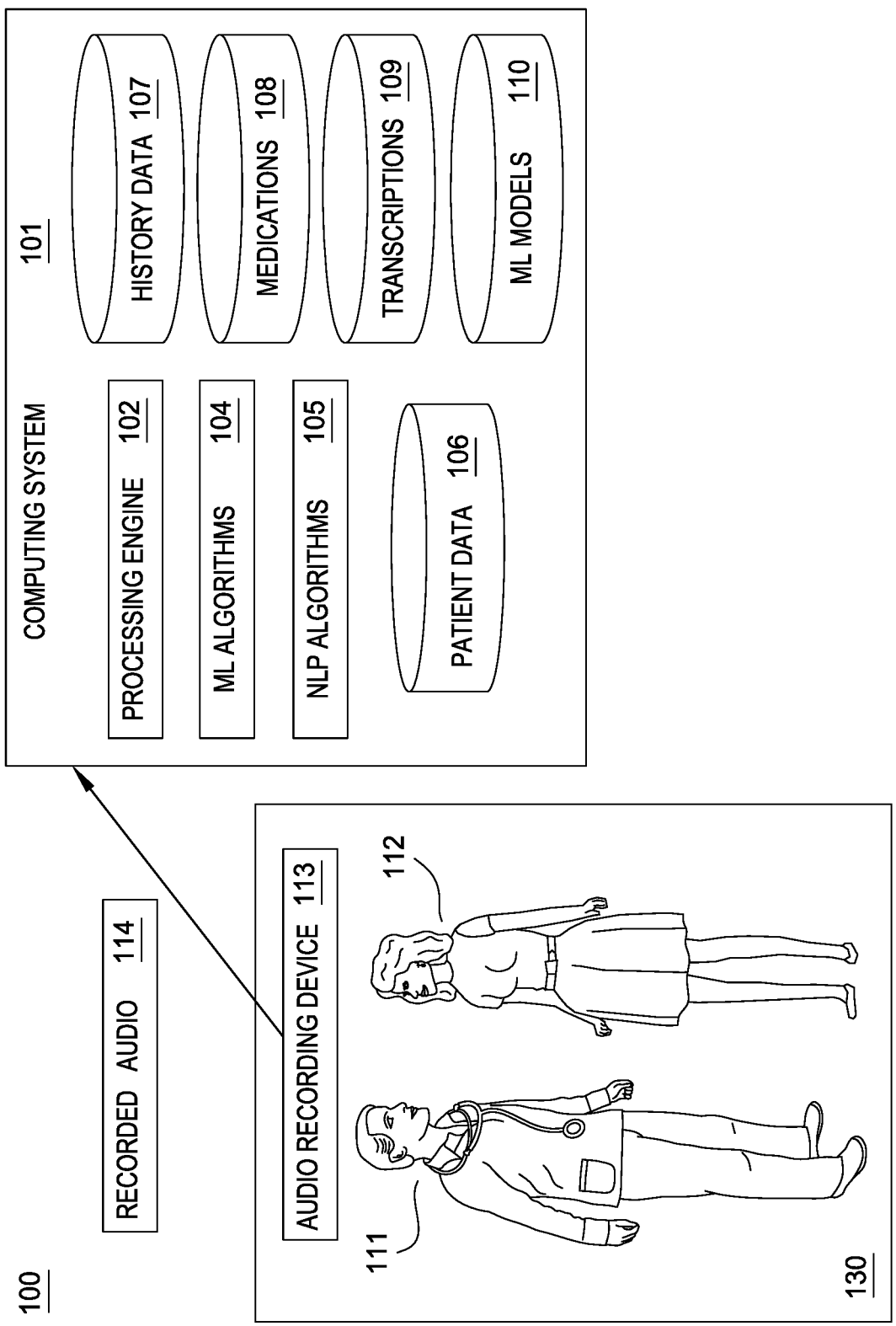
FIG. 1 illustrates a system configured to generate medication orders from a clinical encounter, according to one embodiment.

FIG. 1 illustrates an example system 100 configured to generate medication orders from a clinical encounter, according to one embodiment. As shown, the system 100 includes a computing system 101 and an example clinical environment 130. The clinical environment 130 is representative of any type of patient care setting, such as a hospital, physician's office, in-home consultation, and the like. The clinical environment 130 illustratively includes a medical professional 111 and a patient 112. An audio recording device 113 in the clinical environment 130 records audio of the encounter between the medical professional 111 and the patient 112, and transmits the recorded audio 114 to the computing system 101 in real-time (e.g., via a network).

As shown, the computing system 101 includes a processing engine 102, one or more ML algorithms 104, one or more NLP algorithms 105, and data stores of patient data 106, history data 107, medications 108, transcriptions 109, and ML models 110. The patient data 106 stores information for a plurality of patients, such as biographical information, electronic medical records (e.g., reflecting medical conditions, procedures, etc.), and any other type of medical information. The history data 107 reflects past orders for medications 108 by medical professionals, which may include information indicating geographical and/or organizational preferences for certain types of medications 108. The medications 108 is a knowledge base storing information describing any type of medication information, including without limitation, prescription medicines, over the counter medicine, home remedies, physical therapy orders, stretches, exercises, etc. The transcriptions 109 store annotated transcriptions generated based on audio recordings of clinical encounters between a medical professional and a patient. The ML models 110 store machine learning models reflecting a medical professional's speech patterns, prescription histories, and the like. In at least one embodiment, an ML model 110 for a given medical professional is generated based at least in part on the transcriptions 109 of the speech (or dialogue) of the medical professional. The training of the ML models 110 considers attributes of the speech and/or dialogue of each medical professional (e.g., grammatical features, semantic features, sentiment features, etc.), how the medical professional refers to medications (e.g., by brand name, generic name, etc.), prescription history, and the like. As such, the ML models 110 are used to generate one or more candidate medications from the medications 108 corresponding to a medication a medical professional is referring to in a recorded audio dialogue of a clinical encounter.

In at least one embodiment, a patient may schedule an appointment to visit a medical professional. In such embodiments, the processing engine 102 may reference the patient data 106 to determine the patient's clinical history, which may include a reason for the scheduled appointment, and any medications 108 the patient is currently taking and/or previously was taking. The processing engine 102 may leverage the medication history, patient history, and reason for the appointment to determine a first set of candidate medications 108 that may be prescribed by the medical professional. For example, if the patient's nausea is reason for the visit, the processing engine 102 may identify anti-nausea medications 108 as part of the first set of candidate medications.

At the time of the patient's encounter with a medical professional, the recording device 113 records the conversation, and transmits the audio recording 114 to the computing system 101. The processing engine 102 then generates a transcription of the recorded audio 114 and extracts medication information therefrom. Generally, the processing engine 102 applies speech-to-text NLP algorithms 105 to generate a text transcription of the recorded audio 114. The processing engine 102 may then apply additional NLP algorithms 105 and/or ML algorithms 104 to extract grammatical features of the dialogue (e.g., identify tone, identify sentiment, etc.), eliminate noise, identify references to medications, generate annotations, identify concepts, and extract candidate medications from the transcription. The processing engine 102 may store the annotated transcription (and any other extracted features and/or metadata) in the transcriptions 109. Doing so allows the processing engine 102 to compare what a given medical professional stated during a conversation to what was actually done (e.g., a physician states that she will prescribe a generic class of medication, then prescribes medication N from the class as reflected in the patient data 106 and/or annotations to the transcription).

The ML algorithms 104 and/or NLP algorithms 105 may further reference the history data 107 to identify patterns in medication orders made by the medical professional (e.g., the medical professional often prescribes medication Y when patients have nausea). In at least one embodiment, the processing engine 102 adds the medications 108 that the medical professional most frequently recommends for the patient's condition as candidate medications. Doing so allows the processing engine 102 to generate more accurate candidate medication recommendations.

The processing engine 102 may further rank each statement in the transcript to identify their relative importance as determined by one or more of the ML algorithms 104, NLP algorithms 105, and/or ML models 110. For example, if the transcript includes a single sentence where the medical professional mentions a prescription medication, the processing engine 102 may rank this sentence as the most important. The processing engine 102 may then provide the text transcription to the ML model 110 for the medical professional, which processes the text to identify intent, speech patterns, etc., in the medical professional's dialogue. The ML model 110 may then determine the meaning (e.g., context, tone, sentiment) of each statement made by the medical professional. For example, the ML model 110 may map the phrase "beta-blocker" made by the medical professional to "1 mg beta-blocker Y", as the ML model 110 is tailored to the history of statements made by the medical professional (e.g., the medical professional frequently prescribes beta-blocker Y in 1 mg doses).

The processing engine 102, ML algorithms 104, NLP algorithms 105, and/or ML model 110 may then return a final set of candidate medications from the medications 108 to the medical professional. The medical professional may then select one or more candidate medications 108, and optionally provide feedback regarding the candidates. The feedback may be stored as metadata to the transcription 109 of the audio recording 114. The ML models 110 may be retrained based on the feedback. Furthermore, for each candidate medication 108 selected by the medical professional, the processing engine 102 may transmit an indication via a network. For example, the processing engine 102 may transmit an indication of a prescribed medication 108 to a pharmacy for the patient, while transmitting an email to the patient describing physical therapy exercises for the patient to attempt at home.

FIG. 2A illustrates an example text transcription 109 generated based on an audio recording 114 of a clinical encounter between a medical professional and a patient, according to one embodiment. The transcription 109 depicted in FIG. 2A is a speech-to-text transcription generated by the NLP algorithms 105, where each word spoken during the encounter is transcribed into text. As previously stated, however, the transcription 109 is further processed by the ML algorithms 104, NLP algorithms 105, and/or ML model 110 to remove noise, rank statements, identify concepts, and the like.

FIG. 2B illustrates an annotated text transcription 109. As shown, the text transcription 109 has been annotated with statements of sentiment in brackets. At least some portions of the text of the transcription 109 have been modified to reflect the relative importance of each portion of text. For example, statements that are of little clinical value and do not provide details on the topic of conversation are italicized, while irrelevant statements (e.g., noise) are removed from the transcription 109 as reflected by the strikethrough. Statements that are of some relevance are ranked higher than the irrelevant statements and statements of little clinical value, and are reflected by standard font in FIG. 2B. Statements that reference medications may receive the highest rank, and are bolded in FIG. 2B. Of the highly ranked statements, the statements that reference medications 108 the patient is currently taking and/or have side effects related to the topic of conversation (e.g., patient's chief complaint) are the most highly ranked.

FIG. 2C illustrates additional annotations to the text transcription 109. As shown, the brackets now include any determined sentiment and/or medical conditions of the corresponding statements 210-213. For example, the statement 210 in the transcription 109 of FIG. 2C includes an annotation reflecting that the doctor was joking, and was not being serious when discussing "medicine Y". This indicates to the ML algorithms 104, NLP algorithms 105, and/or ML models 110 that "medicine Y" is a very low candidate medication. Similarly, when processed by the ML model 110 for the medical professional, this statement will receive little consideration as the ML model 110 specifies that the medical professional has no history of prescribing medicine Y for watching sports, and does not use the phrase "handing out [medicine name]" when referencing a prescription the medical professional is about to prescribe.

For the statement 211, the ML model 110 may identify "let's try increasing the dose" as a common way the medical professional writes a new prescription for an existing medication 108 the patient is currently taking. Furthermore, in statement 211, the statement "I'd rather have you on a higher dose of the beta blockers than putting you on an ACE" may be used by the NLP algorithms 105 and/or ML models 110 to determine intent to increase a dosage of an existing medication. Furthermore, the NLP algorithms 105 and/or ML models 110 may determine that "ACE" is not a class of medications, while determining that the statement actually refers to angiotensin-converting-enzyme inhibitors ("ACEI"), which is a known class of medication. Therefore, the NLP algorithms 105 and/or ML models 110 may eliminate "ACEI" as a candidate medication 108 by identifying the concept of "ACEI" based on the statement that included "ACE". For the statement 212, the ML algorithms 104, NLP algorithms 105, and/or ML models 110 may identify one or more concepts that correspond to instructions for taking medications. Furthermore, because the concepts in statement 212 are in the same conversation context, the ML algorithms 104, NLP algorithms 105, and/or ML models 110 may associate the instructions with the prescription. For the statement 213, the ML algorithms 104, NLP algorithms 105, and/or ML models 110 may identify the term "prescription" to indicate that a prescription should exist. Therefore, the candidate medications 108 are returned to the medical professional via a computing device.

In at least one embodiment, each candidate medication 108 is scored, and ranked according to the score. For example, the "beta blocker" the patient is currently taking may be ranked based on the dosage (e.g., higher doses may be scored/ranked higher than the current dose and/or lesser doses). Other types of beta blockers (e.g. different brands of beta blocker, beta blockers used for other purposes, etc.) may be ranked lower than at least one of the beta blocker the patient is currently taking. The medical professional may then select the appropriate medication, and a prescription identifying the medical professional, the patient, the medication, dose, route (e.g., oral, intravenous, etc.), and any other instructions may be transmitted to a pharmacy for fulfillment. The transcriptions 109 depicted in FIGS. 2A, 2B, and/or 2C may be stored in the transcriptions 109 with an indication of the medication selected by the medical professional. Similarly, the patient data 106 may be updated to reflect the new prescription.

Figure 3:
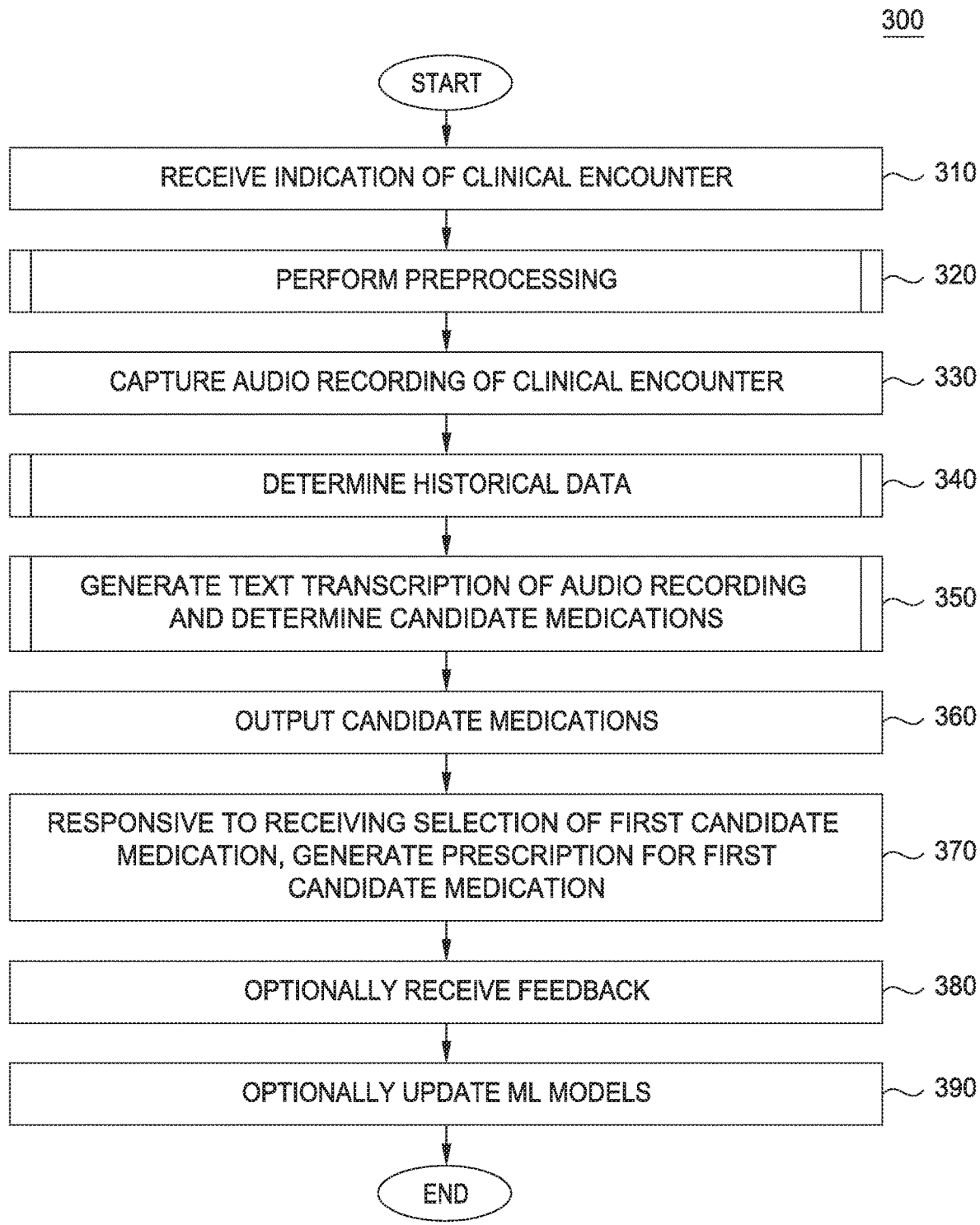
FIG. 3 is a flow chart illustrating a method to generate medication orders from a clinical encounter, according to one embodiment.

FIG. 3 is a flow chart illustrating a method 300 to generate medication orders from a clinical encounter, according to one embodiment. As shown, the method 300 begins at block 310, where the processing engine 102 receives an indication of a clinical encounter between a patient and a medical professional. The indication may reflect a date and time of the clinical encounter, identifiers of the associated patient and medical professional, and one or more complaints and/or problems of the patient. For example, the patient may have a chief complaint of chest pains. At block 320, described in greater detail with reference to FIG. 3, the processing engine 102 optionally performs preprocessing prior to the clinical encounter. The preprocessing may include determining the patient's medical history, medications 108 the patient is currently taking, and any candidate medications 108 that may be prescribed for the current complaints and/or problems of the patient. For example, for the patient having the complaint of chest pains, the preprocessing may determine that the patient has a history of diabetes and hypertension, and takes medications 108 to treat each condition. The preprocessing may identify the diabetes and hypertension medications 108 as candidate medications.

At block 330, the audio recording device 113 captures an audio recording 114 of the dialogue of a clinical encounter between the medical professional and the patient. At block 340, described in greater detail with reference to FIG. 5, the processing engine 102 determines any historical data, which may be related to the medical professional, the patient, the patient's conditions, and the like. For example, the processing engine 102 may determine how the medical professional speaks when he is prescribing medications, and the most frequently prescribed hypertension and/or diabetes medicines the medical professional prescribes. At block 350, described in greater detail with reference to FIG. 6, the processing engine 102 generates a text transcription of the audio recording 114 and determines one or more candidate medications 108. Generally, the processing engine 102 applies ML algorithms 104, NLP algorithms 105, and/or the ML models 110 to generate an annotated text transcription 109 and one or more candidate medications 108 based on the statements in the annotated text transcription 109. For example, the processing engine 102 may return a higher dose of hypertension medicine and a lower dose of the diabetes medicine as the candidate medications 108.

At block 360, the processing engine 102 outputs the candidate medications 108 for display to the medical professional. At block 370, the medical professional provides input selecting a first candidate medication 108, and the processing engine 102 generates a prescription for the first candidate medication. The processing engine 102 may then transmit the prescription to a pharmacy and/or the user. At block 380, the processing engine 102 optionally receives feedback from the medical professional. For example, the feedback may exclude certain medications 108 from further consideration, annotate other medications 108 as preferred medications, and the like. At block 390, the ML models 110 are optionally updated based on the selection of the first prescription, the transcription 109, and any feedback provided by the medical professional.

Figure 4:
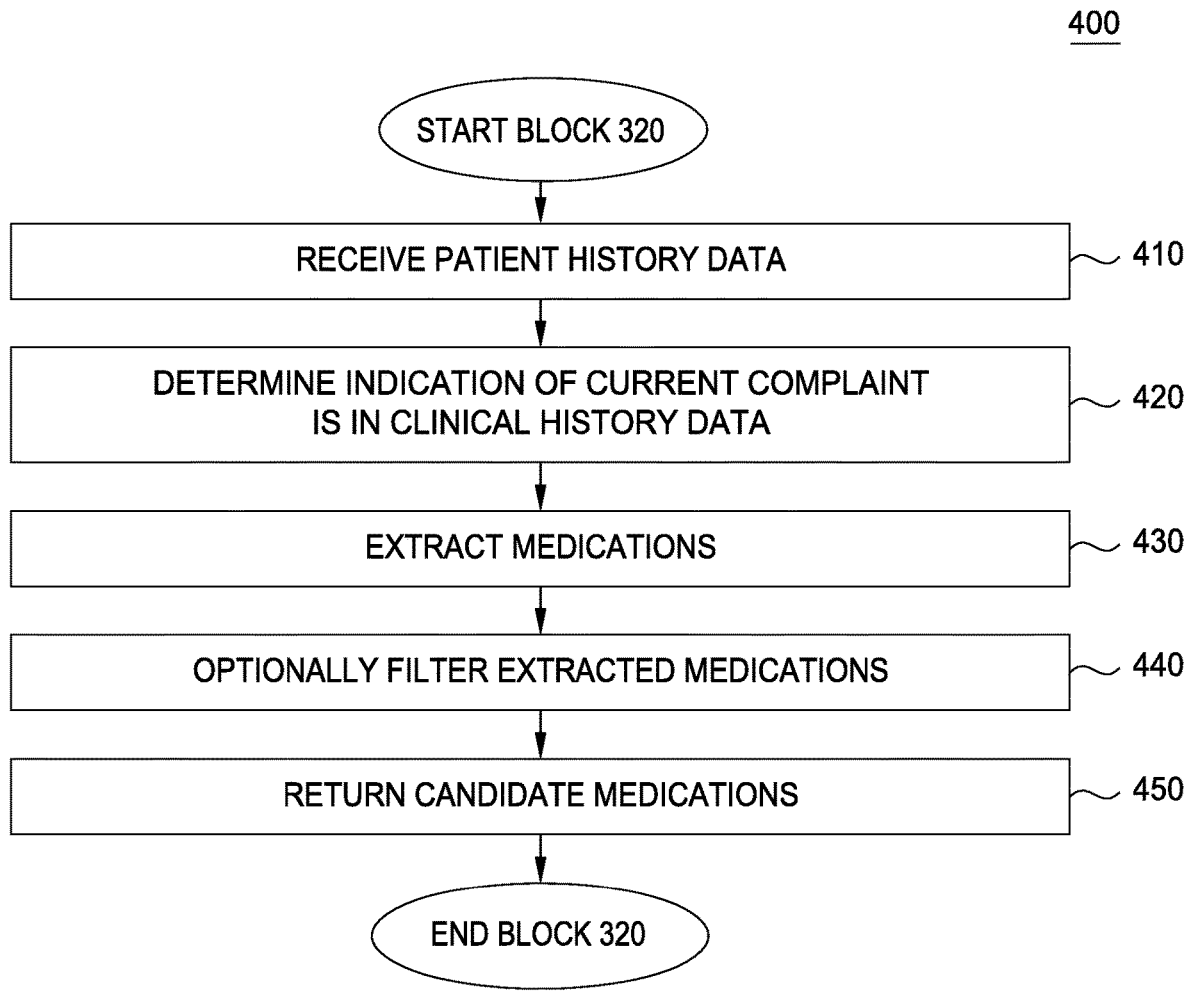
FIG. 4 is a flow chart illustrating a method to perform preprocessing, according to one embodiment.

FIG. 4 is a flow chart illustrating a method 400 corresponding to block 320 to perform preprocessing, according to one embodiment. As shown, the method 400 begins at block 410, where the processing engine 102 receives the patient data 106 for the patient. At block 420, the processing engine 102 determines whether an indication of the current complaint is in the patient data 106. For example, the patient complaining of chest pains may have a history of chest pains as reflected in the patient data 106. At block 430, the processing engine 102 may extract medications 108 that the patient is currently and/or previously has taken from the patient data 106, and extract medications 108 that are most closely related to the patient's complaints (e.g., chest pains). The related medications 108 may be determined based on metadata associated with each medication 108, medical literature, or any other means. At block 440, the processing engine 102 may filter the medications 108 extracted at block 430 based on any number of factors. For example, the processing engine 102 may filter the medications based on known adverse side effects, contraindications, known patient allergies, etc. At block 450, the processing engine 102 returns one or medications 108 as candidate medications for the patient prior to the clinical encounter.

Figure 5:
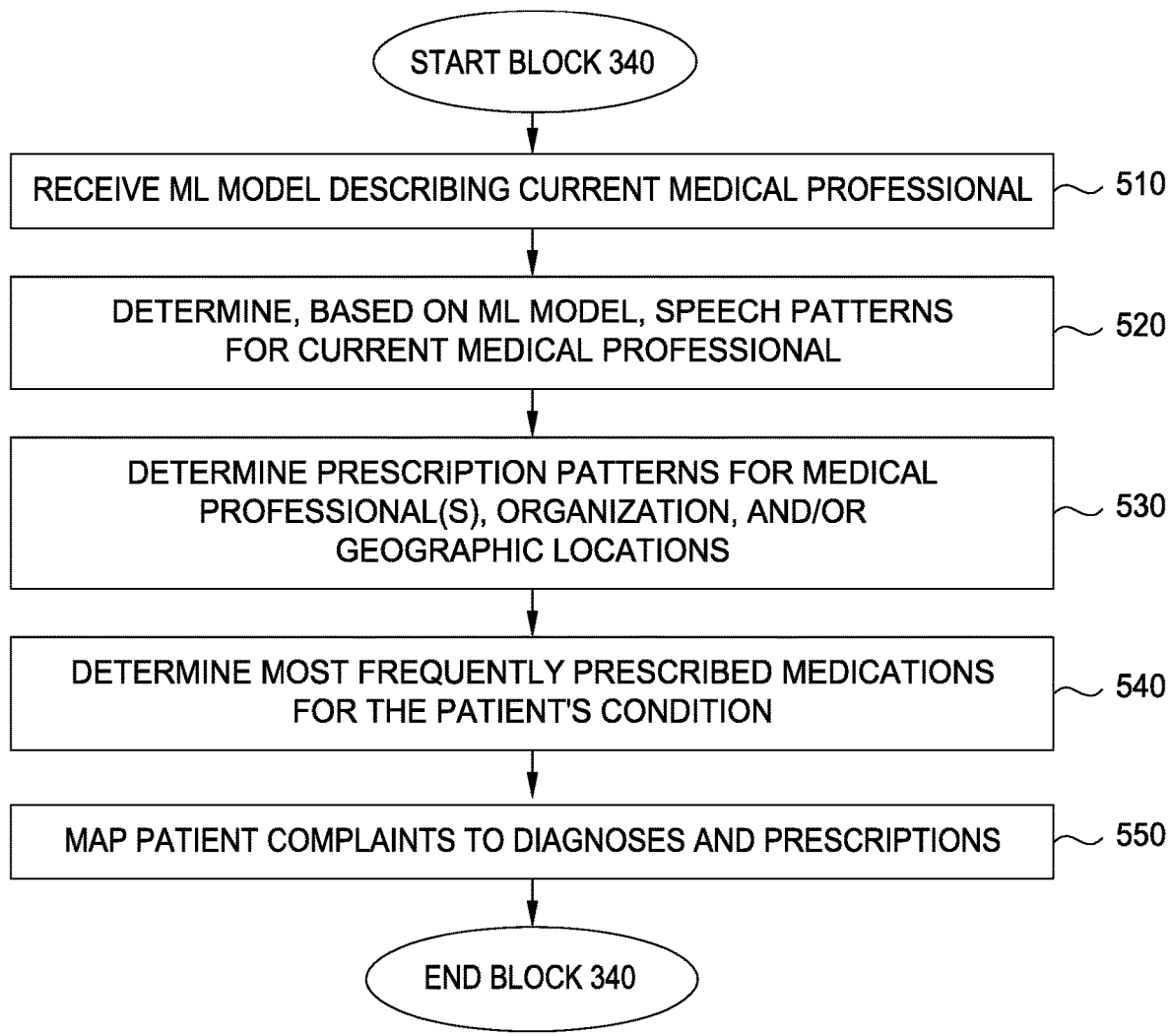
FIG. 5 is a flow chart illustrating a method to determine historical data, according to one embodiment.

FIG. 5 is a flow chart illustrating a method 500 corresponding to block 340 to determine historical data, according to one embodiment. As shown, the method 500 begins at block 510, where the processing engine 102 receives an ML model 110 describing the current medical professional. At block 520, the processing engine 102 determines speech patterns of the medical professional based on the ML model 110. For example, the ML model 110 may specify how the medical professional frequently refers to medications, the medical professional's speech mannerisms, etc. At block 530, the processing engine 102 determines patterns derived for the medical professional specified in the ML model 110 (and/or extracted from the history data). For example, the medical professional may frequently prescribe generic medications. The processing engine 102 may further determine any patterns in the geographic location and/or organization associated with the medical professional. At block 540, the processing engine 102 determines the most frequently prescribed medications for the patient's condition. For example, an electronic medical dictionary may specify which medications are most frequently prescribed for chest pains. At block 550, the processing engine 102 maps each patient complaint to one or more diagnoses and prescriptions.

Figure 6:
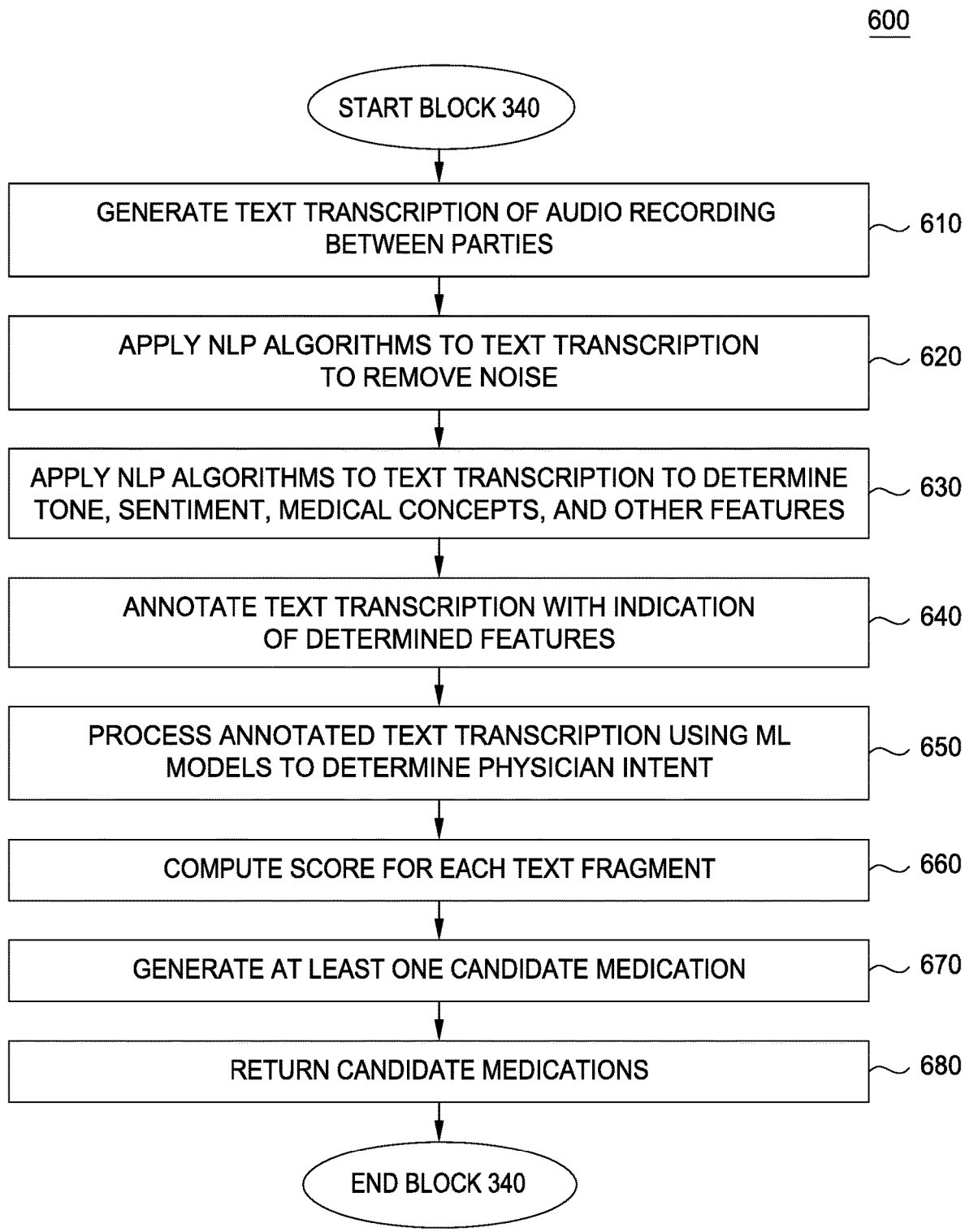
FIG. 6 is a flow chart illustrating a method to generate a text transcription and determine candidate medications, according to one embodiment.

FIG. 6 is a flow chart illustrating a method 600 corresponding to block 350 to generate a text transcription and determine candidate medications, according to one embodiment. As shown, the method 600 begins at block 610, where the processing engine 102 applies one or more NLP algorithms 105 to the audio recording 114 to generate a text transcription. At block 620, the processing engine 102 applies one or more ML algorithms 104, NLP algorithms 105, and or ML models 110 to remove noise from the transcription (e.g., text including concepts that are not related to the patient's medical issues). By removing noise, the processing engine 102 refrains from processing irrelevant statements when generating candidate medications. At block 630, the processing engine 102 applies one or more ML algorithms 104, NLP algorithms 105, and or ML models 110 to determine tone, sentiment, medical concepts, and/or other grammatical features in the text transcription. At block 640, the processing engine 102 annotates the text transcription with indications of the tone, sentiment, medical concepts, and/or other features determined at block 630. At block 650, the text transcription is processed by one or more ML models 110 to determine the intent of the medical professional. For example, the ML model 110 may determine that the medical professional's statement that "you need new pills" means the medical professional will prescribe new medication and/or a different brand of an existing medication.

At block 660, the ML models 110 may compute a score for each fragment (e.g., sentence) of the text transcription. The scores may be computed based on whether the sentence includes medical language, refers to medication and/or prescriptions, and the like. At block 670, the ML models 110 generate at least one candidate medication from the medications 108 based on the text transcription and the intent determined at block 650. For example, based on the patient's complaint, patient history, prescription patterns, and analysis of the text transcription, the ML models 110 may return a ranked list of blood pressure medication for the patient having chest pains. The processing engine 102 may further receive medications 108 related to the candidate medications 108 generated at block 670, e.g., generics, different doses, different brand names, etc. At block 680, the processing engine 102 returns the candidate medications to the medical professional for review.

Figure 7:
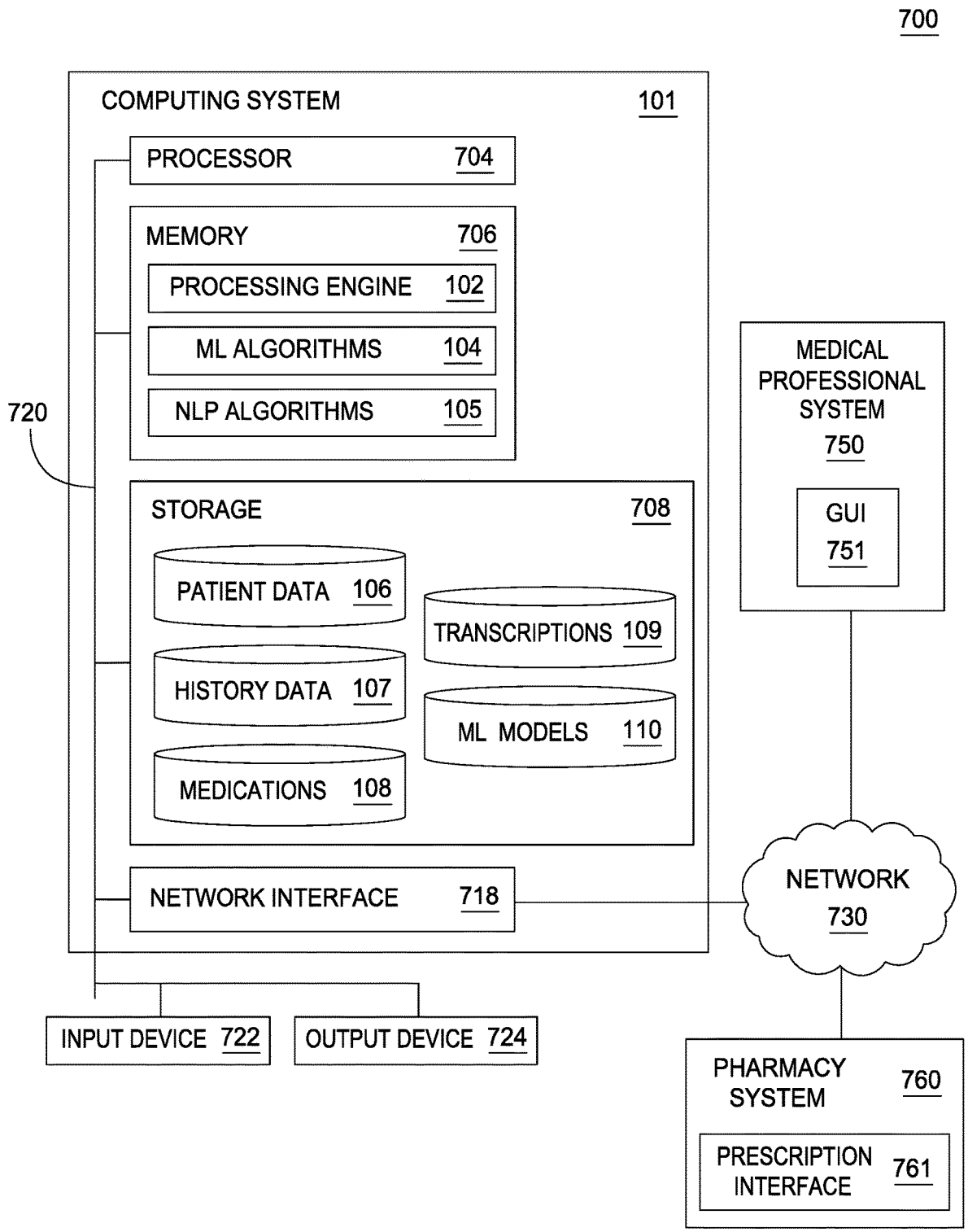
FIG. 7 illustrates a system configured to generate medication orders from a clinical encounter, according to one embodiment.

FIG. 7 illustrates a system 700 configured to generate medication orders from a clinical encounter, according to one embodiment. The networked system 700 includes a computing system 101. The computing system 101 may also be connected to other computers via a network 730. In general, the network 730 may be a telecommunications network and/or a wide area network (WAN). In a particular embodiment, the network 730 is the Internet.

The computing system 101 generally includes a processor 704 which obtains instructions and data via a bus 720 from a memory 706 and/or a storage 708. The computing system 101 may also include one or more network interface devices 718, input devices 722, and output devices 724 connected to the bus 720. The computing system 101 is generally under the control of an operating system (not shown). Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used. The processor 704 is a programmable logic device that performs instruction, logic, and mathematical processing, and may be representative of one or more CPUs. The network interface device 718 may be any type of network communications device allowing the computing system 101 to communicate with other computers via the network 730.

The storage 708 is representative of hard-disk drives, solid state drives, flash memory devices, optical media and the like. Generally, the storage 708 stores application programs and data for use by the computing system 101. In addition, the memory 706 and the storage 708 may be considered to include memory physically located elsewhere; for example, on another computer coupled to the computing system 101 via the bus 720.

The input device 722 may be any device for providing input to the computing system 101. For example, a keyboard and/or a mouse may be used. The input device 722 represents a wide variety of input devices, including keyboards, mice, controllers, and so on. Furthermore, the input device 722 may include a set of buttons, switches or other physical device mechanisms for controlling the computing system 101. The output device 724 may include output devices such as monitors, touch screen displays, and so on.

As shown, the memory 706 contains the processing engine 102, ML algorithms 104, and NLP algorithms 105, each described in greater detail above. The storage 708 contains the patient data 106, history data 107, medications 108, transcriptions 109, and ML models 110, each described in greater detail above. As shown, a medical professional system 750 includes a GUI 751 for outputting candidate medications returned by the processing engine 102, and for receiving selection of candidate medications from the medical professional. Once selected for a prescription, an indication of a prescription for the medication may be transmitted to a prescription interface 761 of a pharmacy system 760.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the foregoing, reference is made to embodiments presented in this disclosure. However, the scope of the present disclosure is not limited to specific described embodiments. Instead, any combination of the recited features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the recited aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications or related data available in the cloud. For example, the processing engine 102 could execute on a computing system in the cloud and generate candidate medication prescriptions for a patient. In such a case, the processing engine 102 could store the text transcriptions 109 at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A computer-implemented method, comprising:
   receiving a plurality of text transcriptions of medical encounters involving a first medical professional;
   training a machine learning (ML) model for the first medical professional based on (i) speech patterns of the first medical professional and (ii) prescription patterns of the first medical professional, based on the plurality of text transcriptions;
   applying one or more natural language processing (NLP) algorithms to a new text transcription of a medical encounter dialogue to determine a plurality of features of the dialogue;
   upon determining, based on the new transcription, that the first medical professional participated in the dialogue, retrieving the ML model trained for the first medical professional;
   processing, by the ML model executing on a processor, the new text transcription and the plurality of features of the dialogue to identify a plurality of candidate medications from a knowledge base, comprising:
      generating a score for each of a plurality of statements made by the first medical professional during the medical encounter; and
      identifying at least one of the plurality of candidate medications based on (i) a first statement of the plurality of statements, (ii) a medication history of a patient involved in the medical encounter, and (iii) a pattern of prescriptions for a geographical location of the medical encounter;
   outputting an indication of the plurality of candidate medications for display;
   receiving feedback from the first medical professional, wherein the feedback specifies to exclude a particular medication from the plurality of candidate medications; and
   updating the ML model based on the feedback.

2. The computer-implemented method of claim 1, wherein the plurality of features comprise: (i) a sentiment, (ii) a tone, (iii) a concept, and (iv) a grammatical feature of each of a plurality of statements in the dialogue, wherein the ML model specifies a plurality of attributes of a speech of the medical professional.

3. The computer-implemented method of claim 2, further comprising:
   determining that the first statement comprises a first concept;
   determining, by the ML model, that the first concept is related to a first type of medication;
   determining, by the ML model, the plurality of candidate medications from the knowledge base based on the first type of medication.

4. The computer-implemented method of claim 1, further comprising:
   receiving selection of a first candidate medication of the plurality of candidate medications;
   generating a prescription for the first candidate medication, wherein the prescription comprises an indication of: (i) a patient associated with the prescription, (ii) a name of the first candidate medication, (iii) a dose of the first candidate medication, (iv) a route of the first candidate medication, and (v) a set of instructions for taking the first candidate medication; and
   transmitting the prescription for fulfillment.

5. The computer-implemented method of claim 1, further comprising:
   capturing an audio recording of the dialogue;
   generating, by the one or more NLP algorithms, the new text transcription of the dialogue; and
   generating, by the one or more NLP algorithms, a plurality of annotations of the new text transcription, wherein the plurality of annotations are processed by the ML model to generate the plurality of candidate medications.

6. The computer-implemented method of claim 1, further comprising:
determining a first set of candidate medications based on a patient history data, a medical condition of a patient, and a prescription history of the medical professional, wherein the first set of candidate medications are processed by the ML model to generate the plurality of candidate medications.

7. The computer-implemented method of claim 1, further comprising:
determining, by the one or more NLP algorithms, that a second statement in the dialogue is not associated with medical concepts; and
discarding the second statement, thereby refraining from processing the second statement by the ML model.

8. A computer program product, comprising:
a non-transitory computer-readable storage medium having computer readable program code embodied therewith, the computer readable program code executable by a processor to perform an operation comprising:
receiving a plurality of text transcriptions of medical encounters involving a first medical professional;
training a machine learning (ML) model for the first medical professional based on (i) speech patterns of the first medical professional and (ii) prescription patterns of the first medical professional, based on the plurality of text transcriptions;
applying one or more natural language processing (NLP) algorithms to a new text transcription of a medical encounter dialogue to determine a plurality of features of the dialogue;
upon determining, based on the new transcription, that the first medical professional participated in the dialogue, retrieving the ML model trained for the first medical professional;
processing, by the ML model, the new text transcription and the plurality of features of the dialogue to identify a plurality of candidate medications from a knowledge base, comprising:
generating a score for each of a plurality of statements made by the first medical professional during the medical encounter; and
identifying at least one of the plurality of candidate medications based on (i) a first statement of the plurality of statements, (ii) a medication history of a patient involved in the medical encounter, and (iii) a pattern of prescriptions for a geographical location of the medical encounter;
outputting an indication of the plurality of candidate medications for display;
receiving feedback from the first medical professional, wherein the feedback specifies to exclude a particular medication from the plurality of candidate medications; and
updating the ML model based on the feedback.

9. The computer program product of claim 8, wherein the plurality of features comprise: (i) a sentiment, (ii) a tone, (iii) a concept, and (iv) a grammatical feature of each of a plurality of statements in the dialogue, wherein the ML model specifies a plurality of attributes of a speech of the medical professional.

10. The computer program product of claim 9, the operation further comprising:

determining that the first statement comprises a first concept;
determining, by the ML model, that the first concept is related to a first type of medication;
determining, by the ML model, the plurality of candidate medications from the knowledge base based on the first type of medication.

11. The computer program product of claim 8, the operation further comprising:
receiving selection of a first candidate medication of the plurality of candidate medications;
generating a prescription for the first candidate medication, wherein the prescription comprises an indication of: (i) a patient associated with the prescription, (ii) a name of the first candidate medication, (iii) a dose of the first candidate medication, (iv) a route of the first candidate medication, and (v) a set of instructions for taking the first candidate medication; and
transmitting the prescription for fulfillment.

12. The computer program product of claim 8, the operation further comprising:
capturing an audio recording of the dialogue;
generating, by the one or more NLP algorithms, the new text transcription of the dialogue; and
generating, by the one or more NLP algorithms, a plurality of annotations of the new text transcription, wherein the plurality of annotations are processed by the ML model to generate the plurality of candidate medications.

13. The computer program product of claim 8, the operation further comprising:
determining a first set of candidate medications based on a patient history data, a medical condition of a patient, and a prescription history of the medical professional, wherein the first set of candidate medications are processed by the ML model to generate the plurality of candidate medications.

14. The computer program product of claim 8, the operation further comprising:
determining, by the one or more NLP algorithms, that a second statement in the dialgo is not associated with medical concepts; and
discarding the second statement, thereby refraining from processing the second statement by the ML model.

15. A system, comprising:
a processor; and
a memory storing one or more instructions which, when executed by the processor, performs an operation comprising:
receiving a plurality of text transcriptions of medical encounters involving a first medical professional;
training a machine learning (ML) model for the first medical professional based on (i) speech patterns of the first medical professional and (ii) prescription patterns of the first medical professional, based on the plurality of text transcriptions;
applying one or more natural language processing (NLP) algorithms to a new text transcription of a medical encounter dialogue to determine a plurality of features of the dialogue;
upon determining, based on the new transcription, that the first medical professional participated in the dialogue, retrieving the ML model trained for the first medical professional;
processing, by the ML model, the new text transcription and the plurality of features of the dialogue to identify a plurality of candidate medications from a knowledge base, comprising:
  generating a score for each of a plurality of statements made by the first medical professional during the medical encounter; and
  identifying at least one of the plurality of candidate medications based on (i) a first statement of the plurality of statements, (ii) a medication history of a patient involved in the medical encounter, and (iii) a pattern of prescriptions for a geographical location of the medical encounter;
outputting an indication of the plurality of candidate medications for display;
receiving feedback from the first medical professional, wherein the feedback specifies to exclude a particular medication from the plurality of candidate medications; and
updating the ML model based on the feedback.

16. The system of claim 15, wherein the plurality of features comprise: (i) a sentiment, (ii) a tone, (iii) a concept, and (iv) a grammatical feature of each of a plurality of statements in the dialogue, wherein the ML model specifies a plurality of attributes of a speech of the medical professional.

17. The system of claim 16, the operation further comprising:
determining that the first statement comprises a first concept;
determining, by the ML model, that the first concept is related to a first type of medication;
determining, by the ML model, the plurality of candidate medications from the knowledge base based on the first type of medication.

18. The system of claim 15, the operation further comprising:
receiving selection of a first candidate medication of the plurality of candidate medications;
generating a prescription for the first candidate medication, wherein the prescription comprises an indication of: (i) a patient associated with the prescription, (ii) a name of the first candidate medication, (iii) a dose of the first candidate medication, (iv) a route of the first candidate medication, and (v) a set of instructions for taking the first candidate medication; and
transmitting the prescription for fulfillment.

19. The system of claim 15, the operation further comprising:
capturing an audio recording of the dialogue;
generating, by the one or more NLP algorithms, the new text transcription of the dialogue; and
generating, by the one or more NLP algorithms, a plurality of annotations of the new text transcription, wherein the plurality of annotations are processed by the ML model to generate the plurality of candidate medications.

20. The system of claim 15, the operation further comprising:
determining a first set of candidate medications based on a patient history data, a medical condition of a patient, and a prescription history of the medical professional, wherein the first set of candidate medications are processed by the ML model to generate the plurality of candidate medications;
determining, by the one or more NLP algorithms, that a second statement in the dialog is not associated with medical concepts; and
discarding the second statement, thereby refraining from processing the second statement by the ML model.

* * * * *